United States Patent
Nakajima et al.

(10) Patent No.: US 10,981,956 B2
(45) Date of Patent: Apr. 20, 2021

(54) NEUROPROTECTIVE PEPTIDE

(71) Applicant: SENJU PHARMACEUTICAL CO., LTD., Osaka (JP)

(72) Inventors: Takeshi Nakajima, Osaka (JP); Mamiko Machida, Osaka (JP); Yujiro Hayashi, Hyogo (JP)

(73) Assignee: SENJU PHARMACEUTICAL CO., LTD., Osaka (JP)

( * ) Notice: Subject to any disclaimer, the term of this patent is extended or adjusted under 35 U.S.C. 154(b) by 199 days.

(21) Appl. No.: 16/087,783

(22) PCT Filed: Mar. 30, 2017

(86) PCT No.: PCT/JP2017/013388
§ 371 (c)(1),
(2) Date: Sep. 24, 2018

(87) PCT Pub. No.: WO2017/170924
PCT Pub. Date: Oct. 5, 2017

(65) Prior Publication Data
US 2020/0299332 A1    Sep. 24, 2020

(30) Foreign Application Priority Data

Mar. 31, 2016   (JP) ............................. JP2016-073287

(51) Int. Cl.
*C07K 14/00* (2006.01)
*A61P 25/28* (2006.01)
*A61K 38/00* (2006.01)

(52) U.S. Cl.
CPC ............ *C07K 14/001* (2013.01); *A61P 25/28* (2018.01); *A61K 38/00* (2013.01)

(58) Field of Classification Search
None
See application file for complete search history.

(56) References Cited

U.S. PATENT DOCUMENTS 6,566,129 B1    5/2003  Borovsky et al.

FOREIGN PATENT DOCUMENTS

| JP | 2010-520851 | 6/2010 |
| JP | 2012-232952 | 11/2012 |
| JP | 2014-510101 | 4/2014 |
| JP | 2014-527057 | 10/2014 |
| WO | 2008/040332 | 4/2008 |
| WO | 2012/127475 | 9/2012 |
| WO | 2013/030111 | 3/2013 |

OTHER PUBLICATIONS

International Search Report dated Jun. 27, 2017 in International (PCT) Application No. PCT/JP2017/013388.
Fung, et al., "Characterization of the in vivo forms of lacrimal-specific proline-rich proteins in human tear fluid", Proteomics, vol. 4; pp. 3953-3959 (2004).
Maruyama S., et al., "Aminopeptidase P, Capable of Hydrolyzing Oligoproline, from Bovine Brain", Biosci. Biotech. Biochem., vol. 58, No. 11, pp. 2107-2108: 0916-8451 (1994).
Yenkoyan K., et al., "Neuroprotective action of proline-rich polypeptide-1 in β-amyloid induced neurodegeneration in rats", Brain Research Bulletin, vol. 86, pp. 262-271: 0361-9230 (2011).
Galoyan A. A., et al., "Protective Effects of Hypothalamic Proline-Rich Peptide and Cobra Venom Naja Naja Oxiana on Dynamics of Vestibular Compensation Following Unilateral Labyrinthectomy", Neurochem. Res.. vol. 35, pp. 1747-1760: 0364-3190 (2010).
Database UniProt [online], Accession No. Q16378, Proline-rich protein 4, May 27, 2002 uploaded, [retrieved on Jun. 19, 2017], Retrieved from the Internet :<URL: http://www.uniprot.org/uniprot/Q16378>, paragraph of 'Sequences (2)', (2002).

*Primary Examiner* — John D Ulm
(74) *Attorney, Agent, or Firm* — Wenderoth, Lind & Ponack, L.L.P.

(57) ABSTRACT

A peptide fragment isolated from proline-rich protein 4 (PRP4) has a neuroprotective action. The peptide can be a neuroprotective drug in a preventive or alleviative pharmaceutical composition. The peptide can be used in a neuropathic treatment.

4 Claims, No Drawings

Specification includes a Sequence Listing.

SEQUENCE LISTING

<160> NUMBER OF SEQ ID NOS: 14

<210> SEQ ID NO 1
<211> LENGTH: 134
<212> TYPE: PRT
<213> ORGANISM: Homo sapiens

<400> SEQUENCE: 1

Met Leu Leu Val Leu Leu Ser Val Val Leu Leu Ala Leu Ser Ser Ala
 1               5                  10                  15

```
Gln Ser Thr Asp Asn Asp Val Asn Tyr Glu Asp Phe Thr Phe Thr Ile
             20                  25                  30

Pro Asp Val Glu Asp Ser Ser Gln Arg Pro Asp Gln Gly Pro Gln Arg
             35                  40                  45

Pro Pro Pro Glu Gly Leu Leu Pro Arg Pro Pro Gly Asp Ser Gly Asn
             50                  55                  60

Gln Asp Asp Gly Pro Gln Gln Arg Pro Pro Lys Pro Gly Gly His His
65                   70                  75                  80

Arg His Pro Pro Pro Pro Phe Gln Asn Gln Gln Arg Pro Pro Gln
                 85                  90                  95

Arg Gly His Arg Gln Leu Ser Leu Pro Arg Phe Pro Ser Val Ser Leu
                100                 105                 110

Gln Glu Ala Ser Ser Phe Phe Arg Arg Asp Arg Pro Ala Arg His Pro
            115                 120                 125

Gln Glu Gln Pro Leu Trp
        130
```

<210> SEQ ID NO 2
<211> LENGTH: 100
<212> TYPE: PRT
<213> ORGANISM: Artificial Sequence
<220> FEATURE:
<223> OTHER INFORMATION: Peptide of PRP4

<400> SEQUENCE: 2

```
Gln Ser Thr Asp Asn Asp Val Asn Tyr Glu Asp Phe Thr Phe Thr Ile
1               5                  10                  15

Pro Asp Val Glu Asp Ser Ser Gln Arg Pro Asp Gln Gly Pro Gln Arg
             20                  25                  30

Pro Pro Pro Glu Gly Leu Leu Pro Arg Pro Pro Gly Asp Ser Gly Asn
             35                  40                  45

Gln Asp Asp Gly Pro Gln Gln Arg Pro Pro Lys Pro Gly Gly His His
             50                  55                  60

Arg His Pro Pro Pro Pro Phe Gln Asn Gln Gln Arg Pro Pro Gln
65                  70                  75                  80

Arg Gly His Arg Gln Leu Ser Leu Pro Arg Phe Pro Ser Val Ser Leu
                 85                  90                  95

Gln Glu Ala Ser
            100
```

<210> SEQ ID NO 3
<211> LENGTH: 14
<212> TYPE: PRT
<213> ORGANISM: Artificial Sequence
<220> FEATURE:
<223> OTHER INFORMATION: Peptide of PRP4

<400> SEQUENCE: 3

```
His Pro Pro Pro Pro Phe Gln Asn Gln Gln Arg Pro Pro
1               5                  10
```

<210> SEQ ID NO 4
<211> LENGTH: 13
<212> TYPE: PRT
<213> ORGANISM: Artificial Sequence
<220> FEATURE:
<223> OTHER INFORMATION: Peptide of PRP4

<400> SEQUENCE: 4

His Pro Pro Pro Pro Pro Phe Gln Asn Gln Gln Arg Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Peptide of PRP4

<400> SEQUENCE: 5

His Pro Pro Pro Pro Pro Phe Gln Asn Gln Gln Arg
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Peptide of PRP4

<400> SEQUENCE: 6

His Pro Pro Pro Pro Pro Phe Gln Asn Gln Gln
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Peptide of PRP4

<400> SEQUENCE: 7

His Pro Pro Pro Pro Pro Phe Gln Asn Gln
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Peptide of PRP4

<400> SEQUENCE: 8

His Pro Pro Pro Pro Pro Phe Gln Asn
1               5

<210> SEQ ID NO 9
<211> LENGTH: 8
<212> TYPE: PRT
<213> ORGANISM: Artificial Sequence
<220> FEATURE:
<223> OTHER INFORMATION: Peptide of PRP4

<400> SEQUENCE: 9

His Pro Pro Pro Pro Pro Phe Gln
1               5

<210> SEQ ID NO 10
<211> LENGTH: 7
<212> TYPE: PRT
<213> ORGANISM: Artificial Sequence
<220> FEATURE:
<223> OTHER INFORMATION: Peptide of PRP4

<400> SEQUENCE: 10

His Pro Pro Pro Pro Pro Phe

```
<210> SEQ ID NO 11
<211> LENGTH: 6
<212> TYPE: PRT
<213> ORGANISM: Artificial Sequence
<220> FEATURE:
<223> OTHER INFORMATION: Peptide of PRP4

<400> SEQUENCE: 11

His Pro Pro Pro Pro Pro
1               5

<210> SEQ ID NO 12
<211> LENGTH: 16
<212> TYPE: PRT
<213> ORGANISM: Artificial Sequence
<220> FEATURE:
<223> OTHER INFORMATION: peptide of PRP4

<400> SEQUENCE: 12

His Pro Pro Pro Pro Pro Phe Gln Asn Gln Gln Arg Pro Pro Gln Arg
1               5                   10                  15

<210> SEQ ID NO 13
<211> LENGTH: 19
<212> TYPE: PRT
<213> ORGANISM: Artificial Sequence
<220> FEATURE:
<223> OTHER INFORMATION: peptide of PRP4

<400> SEQUENCE: 13

His Pro Pro Pro Pro Pro Phe Gln Asn Gln Gln Arg Pro Pro Gln Arg
1               5                   10                  15

Gly His Arg

<210> SEQ ID NO 14
<211> LENGTH: 5
<212> TYPE: PRT
<213> ORGANISM: Artificial Sequence
<220> FEATURE:
<223> OTHER INFORMATION: Peptide of PRP4

<400> SEQUENCE: 14

Gln Gln Arg Pro Pro
1               5
```

NEUROPROTECTIVE PEPTIDE

FIELD

The present invention relates to a peptide which has a neuroprotective action, a neuroprotective agent comprising the peptide and a pharmaceutical composition for treating or preventing nerve damage, comprising the peptide.

BACKGROUND

Nerve cells are cells that constitute the nervous system, which can be broadly divided into the central nervous system and the peripheral nervous system. Nerve cells are prone to be damaged by external factors such as a cerebrovascular injury such as a stroke, a brain infarction, etc.; or internal factors such as an accumulation of abnormal proteins, oxidant stress, inflammation, etc., while their regenerative capacity is low. Thus, once nerve cells are damaged, those damaged nerve cells cause a marked reduction in the QOL of a patient. Neurodegenerative disorders that involve degeneration and loss of nerves of the central nervous system, include neurodegenerative diseases such as Alzheimer's disease, Parkinson's disease. Huntington's disease, amyotrophic lateral sclerosis, multiple sclerosis, etc. as well as degenerative diseases of the optic nerve such as glaucoma, etc.; and neurosensory degenerative diseases such as neural hearing loss, etc.

With developments in neuro science, various neuroprotective factors have been discovered, and they are expected to developed as a drug for preventing or treating nerve damage. While agents that reduce free radicals or excitatory amino acids and agents that can protect and/or repair nerve cells (e.g., immunophilin ligands such as neurotrophic factors and immunosuppressants) have been found to have a neuroprotective action, it has also been found that biological proteins, such as pituitary adenylate cyclase-activating polypeptide (PACAP). CD44 and human brain carboxypeptidase B (HBCPB), have a neuroprotective action. (PTL 1 and 2)

Human tears contain numerous proteins such as lysozymes, lactoferrins, etc., which serve to maintain the homeostasis of the corneal surface. Moreover, tears also contain degradants of proteins, and it is expected that such peptide fragments have various actions. Proline-rich protein 4(PRP4) known to be present in tears is a protein having a full amino acid length of 134 residues. Since it has an antibacterial action, it is suggested that it acts as a protective mechanism against pathogens in mucous tissues (NPL 1).

CITATION LIST

Patent Literature

[PTL 1] JP 2014-510101
[PTL 2] JP 2012-232952
Non-Patent Literature
[NPL1] Proteomics 2004, 4, 3953-3959

SUMMARY

Technical Problem

The purpose of the present invention is to provide a novel peptide which has a neuroprotective action, and a composition for treating or preventing nerve damage comprising the peptide.

Solution To Problem

The present inventors discovered dial proline-rich protein 4 (PRP4) and peptide fragments isolated therefrom, have a neuroprotective action, and thereby completed the present invention.

The present invention relates to the following;
[1] A peptide consisting of the amino acid sequence of HPPPPPFQNQQRPP (SEQ ID NO; 3) or a terminal-deleted sequence thereof, wherein;
the terminal-deleted sequence consisting of:
1) a sequence derived from SEQ ID NO: 3 by deletion of 1 to 8amino acids fr om the C-terminal thereof, and/or
2) a sequence derived from SEQ ID NO: 3 by deletion of one or two amino acids from the N-terminal of SEQ ID NO:3:
wherein the peptide consisting of a terminal-deleted sequence has a neuroprotective action.
[2] The peptide according to item 1, wherein tbe number of C-terminal amino acids deleted is 1 to 6.
[3] A peptide consisting of tbe amino acid sequence of HPPPPPFQ (SEQ ID NO: 9) or an amino acid sequence derived therefrom by addition of one or two amino acids to the N-terminal, the C-terminal or both terminals thereof, wherein the peptide has a neuroprotective action.
[4] A peptide consisting of the amino acid sequence of HPPPPPFQNQQ (SEQ ID NO: 6) or an amino acid sequence derived therefrom by addition of one or two amino acids to the N-terminal. the C-terminal or both terminals thereof, wherein the peptide has a neuroprotective action.
[5] A peptide consisting of the amino acid sequence of HPPPPPFQNQQRPP (SEQ ID NO: 3) or an amino acid sequence derived therefrom by addition of one or two amino acids to the N-terminal, the C-terminal or both terminals thereof, wherein the peptide has a neuroprotective action.
[6] The peptide according to any one of items 3 to 5, wherein one or two amino acids are added to the C-terminal.
[7] A neuroprotective agent comprising the peptide according to any one of items 1 to 6.
[8] A neuroprotective agent comprising a peptide consisting of the amino acid sequence of SEQ ID NO: 1 or SEQ ID NO: 2 or a modified sequence thereof, wherein the modified sequence is:
1) a sequence derived from the original sequence by substitution, deletion or addition of one or several amino acids, or
2) a sequence having at least 90% sequence identity to the original sequence; wherein the peptide consisting of the modified sequence has a neuroprotective action.
[9] A neuroprotective agent comprising a peptide consisting of an amino acid sequence derived from the sequence of SEQ ID NO: 3 by addition of one or more amino acids to the N-terminal, the C-terminal or both terminals thereof; wherein the peptide consists of a terminal-deleted sequence of SEQ ID NO: 2 and has a neuroprotective action.
[10] The neuroprotective agent according to item 9, wherein the number of amino acids added to the N-terminal is 1 to 65. and/or the number of amino acids added to the C-terminal is 1 to 21.
[11] A pharmaceutical composition for treating or preventing nerve damage, comprising the neuroprotective agent according to any one of items 7 to 10.

[12] A method of treating or preventing nerve damage, comprising administering the neuroprotective agent according to items 7 to 10, to a subject having nerve damage.
[13] The peptide according to any one of items 1 to 6 or a peptide consisting of the sequence of SEQ ID NO: 1 or SEQ ID NO: 2. or a modified sequence thereof, or a terminal-deleted sequence of SEQ ID NO: 2, for use in treating or preventing nerve damage or in nerve protection.
[14] Use of the peptide according to any one of items 1 to 6 or a peptide consisting of the sequence of SEQ ID NO: 1 or SEQ ID NO: 2, or a modified sequence thereof, or a terminal-deleted sequence of SEQ LD NO: 2, for the manufacture of a therapeutic agent or a preventive agent for nerve damage.
[15] The pharmaceutical composition according to item 11, the method according to item 12.the peptide according to item 13, or the use according to item 14, wherein the nerve damage is a neurodegenerative disease or a cerebrovascular disorder.
[16] The pharmaceutical composition, method, peptide or use according to item 15, wherein the neurodegenerative disease is selected from the group consisting of dementia, Parkinson's disease, spinocerebellar degeneration, Creutzfeldt-Jakob disease, Alzheimer's disease. Huntington's chorea, multiple sclerosis, mad cow disease, spinal progressive muscular atrophy, amyotrophic lateral sclerosis, spinal and bulbar muscular atrophy, glaucoma, retinal pigmentary degeneration, age-related macular degeneration, diabetic retinopathy, hearing loss and epilepsy.
[17] The method according to item 12, the peptide according to item 13, or the use according to item 14 for treating or preventing nerve damage through nerve protection.

Advantageous Effects of Invention

A peptide of the present invention inhibits the death of nerve cells, and consequently has a neuroprotective action. Therefore, a peptide according to the present invention can be used in the treatment or prevention of nerve damage. Moreover, since a peptide according to the present invention is a fragment of protein present in human tears, it can be developed as a medicine with low side effects because it has low toxicity and low immunogenicity when used in a living body.

DESCRIPTION OF EMBODIMENTS

The present invention relates to a peptide consisting of proline-rich protein 4 having the sequence of SEQ ID NO: 1 or a partial sequence thereof, or a modified sequence thereof, which has a neuroprotective action. In a preferred aspect, it is preferable that such a peptide be an isolated and/or purified peptide. The phrase "isolated and/or purified peptide" is intended to refer to a substantially isolated peptide of interest and to distinguish it from a peptide merely existing as a mixture in an unseparated state, such as in a body fluid or in a mixture following protease treatment for analysis.

TABLE 1

| Name | Sequence |
| --- | --- |
| PRP4 | MLLVLLSVVLLALSSAQSTDNDVNYEDFTFTIPDVEDSSQRPD QGPQRPPPEGLLPRPPGDSGNQDDGPQQRPPKPGGHHRHPPPP |

TABLE 1-continued

| Name | Sequence |
| --- | --- |
| | PFQNQQRPPQRGHRQLSLPRFPSVSLQEASSFFRRDRPARHPQ EQPLW (SEQ ID NO: 1) |

In one situation, in one aspect of the present invention, a peptide of the present invention is a peptide having the sequence of SEQ ID NO: 2 or a partial sequence thereof, or a peptide consisting of a modified sequence thereof, and having an amino acid length of 50 to 200 residues. It is more desirable that such a peptide comprise, for example, 80 to 150 amino acid residues, it is particularly desirable that it comprise 90 to 140 amino acid residues, and it is even more desirable that it comprise 100 to 140 amino acid residues. Such a long-chain peptide can exhibit neuroprotective action in that state or can produce a peptide of the present invention through the action of protease in the living body to exhibit neuroprotective action. As an example, a peptide (PRR4 (human) recombinant protein, catalog number: H0001127), which is marketed by Abnova Corporation, comprising the amino acid sequence of position 17 to position 116 (SEQ ID NO: 2) of proline-rich protein 4 can be used.

TABLE 2

| Name | Sequence |
| --- | --- |
| PRP4 (position 17 to position 116) | QSTDNDVNYEDFTFTIPDVEDSSQRP DQGPQRPPPEGLLPRPPGDSGNQDDG PQQRPPKPGGHHRHPPPPPFQNQQRP PQRGHRQLSLPRFPSVSLQEAS (SEQ ID NO: 2) |

In another aspect of the present invention, the present invention relates to a peptide comprising the amino acid sequence of position 17 to position 116 of an amino acid sequence of proline-rich protein 4 (SEQ ID NO. 1), having a neuroprotective action. Such a peptide may have a sequence to which any amino acids are added to the N-terminal and C-terminal of the amino acid sequence of position 17 to position 116 (SEQ ID NO: 2) of proline-rich protein 4, but it is desirable that the peptide have amino acids corresponding to the full-length sequence (SEQ ID NO: 1). Therefore, the peptide comprising the amino acid sequence of position 17 to position 116 of proline-rich protein 4 is a peptide consisting of the amino acid sequence of SEQ ID NO: 1 or a terminal-deleted sequence thereof, wherein the terminal-deleted sequence is a sequence:
1) derived from the original sequence by deletion of 1 to 16 N-terminal amino acids, and/or
2) derived from the original sequence by deletion of 1 to 18 C-terminal amino acids,
and the peptide consisting of the terminal-deleted sequence has a neuroprotective action. Therefore, such a peptide comprises 100 to 134 amino acid residues.

The modified sequence is a sequence derived from the original sequence by substitution, deletion, or addition of one or several amino adds. It is desirable that the number of amino acids substituted, deleted or added be 1 to 3, preferably 1 or 2, and most preferably 1, so long as the peptide has a neuroprotective action. It is desirable that an amino acid substituted be substituted with an amino acid having the same property. Moreover, the modified sequence refers to a sequence having a predetermined sequence identity to the original sequence, wherein the peptide consisting of the modified sequence can exhibits the function or effect of the peptide consisting of the original sequence. The predetermined sequence identity (BLAST) refers to a sequence identity of at least about 75%, about 80%, about 85%, about 90%, about 95%, about 97%, about 98%, or about 99%.

A peptide having a partial sequence is not limited in particular so long as the peptide has a neuroprotective action. Examples of the partial sequence include a sequence without a signal sequence, a terminal-deleted sequence without an N-terminal sequence and or a C-terminal sequence, winch does not contribute to the activity, and a sequence contributing to the activity. So long as the partial sequence has neuroprotective action, it may be of any length. For example, it may have an amino acid length of 4 to 133.

In another situation, in one aspect of the present invention, the present invention relates to a peptide consisting of the sequence of HPPPPPFQNQQRPP (SEQ ID NO: 3) or a sequence derived therefrom by deletion of one or several amino acids from the N-terminal, C-terminal or both terminals thereof. In the case of the deletion from the C-terminal, the number of amino acids deleted can be arbitrarily selected from 1 to 8, so long as the peptide has a neuroprotective action. From the perspective of not affecting the neuroprotective action of the original peptide, 1 to 7 amino acids is/are preferably deleted, more preferably 1 to 6 amino acids are deleted and most preferably 3 or 6 amino acids are deleted. In the case of the deletion from the N-terminal, one or two amino acids are deleted. From the perspective of maintaining the neuroprotective action, a peptide having a sequence with deletion from tire C-terminal is desirable. Preferable peptides according to the present invention are listed below, but this list is not intended to limit the present invention to these peptides.

TABLE 3

| Peptide sequence |
|---|
| HPPPPPFQNQQRPP (SEQ ID NO: 3) |
| HPPPPPFQNQQRP (SEQ ID NO: 4) |
| HPPPPPFQNQQR (SEQ ID NO: 5) |
| HPPPPPFQNQQ (SEQ ID NO: 6) |
| HPPPPPFQNQ (SEQ ID NO: 7) |
| HPPPPPFQN (SEQ ID NO: 8) |
| HPPPPPFQ (SEQ ID NO: 9) |
| HPPPPPF (SEQ ID NO: 10) |
| HPPPPP (SEQ ID NO: 11) |

In another aspect of the present invention, the present invention relates to a peptide consisting of the sequence of HPPPPPFQ (SEQ ID NO: 9) or a sequence derived therefrom by addition of 1 or more amino acids to the N-terminal, C-terminal or both terminals thereof. More preferably, the present invention relates to a peptide consisting of the sequence of HPPPPPFQNQQ (SEQ ID NO: 6) or a sequence derived therefrom by addition of one or several amino acids to the N-terminal, C-terminal or both terminals thereof. Even more preferably, the present invention relates to a peptide consisting of the sequence of HPPPPPFQNQQRPP (SEQ ID NO: 3) or a sequence derived therefrom by addition of one or several amino acids to the N-terminal, C-terminal or both terminals thereof. So long as the peptide has a neuroprotective action, the amino acid added may be any amino acid. From the perspective of not affecting the neuroprotective action of the original peptide, 1 or 2 amino acids are preferably added, and more preferably, 1 amino acid is added. The amino acid added may be of any amino acids, but it is preferable that the amino acid has the same property as an amino acid corresponding to the amino acid sequence (SEQ ID NO: 2) of commercially available proline-rich protein 4.

In another aspect of the present invention, the present invention relates to a peptide consisting of the sequence of HPPPPPFQNQQRPP (SEQ ID NO: 3) or a sequence derived therefrom by addition of amino acids to the N-terminal, C-terminal or both terminals thereof. It is preferable that the amino acids added to the N-terminal of SEQ ID NO: 3 be amino acids corresponding to positions 1 to 65 of the sequence of the amino acid sequence (SEQ ID NO. 2) of a commercially available proline-rich protein 4 peptide, and amino acids added to the C-terminal of SEQ ID NO: 3 be amino acids corresponding to positions 80 to 100 of the amino acid sequence (SEQ ID NO: 2) of a commercially available proline-rich protein 4 peptide. Therefore, the peptide can be considered to be a peptide consisting of a terminal-deleted sequence of the sequence of SEQ ED NO: 2. Such a terminal-deleted sequence is a sequence derived from SEQ ID NO: 2 by deletion of 1 to 65 amino acids, preferably 1 to 40 amino acids, more preferably 1 to 20 amino acids, and even more preferably 1 to 10 amino acids from the N-terminal of SEQ ID NO: 2, and or deletion of 1 to 21 amino acids, preferably 1 to 10 amino acids, preferably 1 to 5 amino acids from the C-terminal of SEQ ID NO: 2. The number of amino acids added to the N-terminal of the sequence of SEQ ID NO: 3 can be arbitrarily selected from 1 to 65, so long as the peptide has a neuroprotective action, and preferably 1 to 30 amino acids are added, more preferably 1 to 20 amino acids are added, even more preferably 1 to 10 amino acids are added, and most preferable 1 to 5 amino acids are added. The number of amino acids added to the C-terminal of the sequence of SEQ ID NO: 3 can be freely selected from 1 to 21, so long as the peptide has a neuroprotective action, and preferably 1 to 10 amino acids are added, and most preferably 1 to 5 amino acids are added. From the perspective of maintaining the neuroprotective action, a peptide having a sequence with amino acid addition to the C-terminal is preferable. Of sequences with such amino acid addition, peptides consisting of the amino acid sequence of positions 82 to 97 and consisting of the amino acid sequence of positions 82 to 100 (SEQ ID NO: 12 and SEQ ID NO: 13) of the PRP4 amino acid sequence (SEQ ID NO: 1) can be excluded from the present invention.

TABLE 4

| Peptide sequence |
|---|
| HPPPPPFQNQQRPPQR (SEQ ID NO: 12) |
| HPPPPPFQNQQRPPQRGHR (SEQ ID NO: 13) |

The phrase "amino acid having the same property" means an amino acid having a side chain of the same property. For example, amino acids that have non-polar side chains include, for example, glycine, alanine, valine, leucine, isoleucine, methionine, proline, phenylalanine, tryptophan; amino acids that have polar side chains include, for example, serine, threonine, asparagine, glutamine, tyrosine, cysteine;

amino acids that have basic side chains include, for example, lysine, arginine, histidine; and amino acids that have acid side chains includes, for example, aspartic acid, glutamic acid.

Generally, the shorter the peptide, tire higher its permeability across the blood-brain barrier or the blood-retinal barrier, and moreover, the easier its synthesis is. On the other hand, a certain length is required from the perspective of securing a neuroprotective action. A peptide of the present invention has a neuroprotective action and high in vivo stability, in particular in a vitreous body. It is preferable that high in vivo stability is preferable in terms of exhibiting a neuroprotective action for a long period at a small dose. Since the peptide has high stability in particular in a vitreous humor solution, it can have a neuroprotective action over a long period of time in a vitreous body by administration through intravitreal injection.

The peptide according to the present invention can lie prepared by any manufacturing process. For example, it can be prepared by carrying out a solid-phase synthesis or a liquid-phase synthesis using a Boc method or an Fmoc method, etc. Alternatively, the peptide according to the present invention can be obtained by synthesizing a long-chain peptide consisting of the sequence such as SEQ ID NO: 1 or 2, which comprising the peptide according to the present invention, in host cells by using a gene transfer method, purifying the long-chain peptide by means of a polyhistidine tag or the like, and then, cleaving the resulting long-chain peptide.

The peptide according to the present invention encompasses derivatives in which the N-terminal amino group, the C-terminal carboxy group or a functional group of an amino acid side-chain has been arbitrarily modified, so long as the neuroprotective action is not lost. Examples of modification include the addition of a protecting group to an amino group (e.g., acetylation, formylation, Boc-protection, Fmoc-protection), the esterification of a carboxyl group (e.g., ethylation), etc. Moreover, modification may include modification that normally occurs in the living body such as phosphorylation, amidation, methylation, esterification, acetylation, etc., modification that occurs during the process of synthesis or facilitates purification such as biotinylation. Moreover, modification such as PEGylatiomn may be added for the purpose of prolonging the half-life of a peptide.

The peptide according to the present invention includes a pharmaceutically acceptable salt. Examples of the pharmaceutically acceptable salt include salts formed with an inorganic acid (e.g., a hydrochloride salt, a hydrobromide salt, a sulfate, and a phosphate) and salts formed with an organic acid (a methanesulfonate, a benzene sulfonate, a p-toluenesulfonate, a formate, an acetate, a trifluoracetate, an oxalate, a citrate, a malonate, a fumarate, a maleate, a tartrate, a succinate, malate, etc.) or salts formed with a base (e.g., an aminonium salt, a methyl pyridinium salt, an acetyl pyridinium salt, etc.). The peptide according to the present invention also comprises a hydrate or a solvate.

The neuroprotective agent according to the present invention refers to an agent having a neuroprotective action. Therefore, a neuroprotective agent can protect a nerve from damage of nerve cells, a disorder accompanied by degeneration of nerve cells and/or cell death, and can also be referred to as a nerve cell death (apoptosis and/or necrosis) inhibiting drug, a nerve cell degeneration inhibiting drug, a nerve cell stress mitigating drug, a nerve cell toxicity resistance improving agent, a nerve cell viability improving agent, and an abnormal protein accumulation inhibiting drug.

In the present specification, the term "neuroprotective action" is used to refer to the action of protecting nerve cells from damage, degeneration and/or cell death, and preferably, the term refers to the action of protecting from nerve cell death. More specifically, the term "neuroprotective action" may include the suppression of nerve cell death (apoptosis and/or necrosis), the suppression of nerve cell degeneration, the mitigation of nerve cell stress, the improvement in resistance to nerve cell toxicity, the improvement in the survival viability of nerve cells, the suppression of abnormal protein accumulation, etc. Nerve cells can be damaged by exposure to a neurotoxic substance and a deficiency in oxygen or a nutritional substance, as well as by physical damage, and if the damage exceeds a certain level, nerve cell death is caused.

Moreover, a nerve cell can be subjected to degeneration as a result of an accumulation of a neurotoxic substance, and ultimately nerve cell death is caused. It is shown in Examples that a peptide of the present invention inhibits cell death under hypoxic condition, but a peptide of the present invention does not only inhibit cell death, it has a protective effect against damage or degeneration of nerve cells at the stage prior to that cell-death stage. Therefore, one could say that a peptide according to the present invention has a neuroprotective action against hypoxia-induced stress and nerve cell death. Neurotoxic substances can be mainly divided into exogenous toxic substances and endogenous toxic substances. An exogenous toxic substances includes chemical substances such as a heavy metal, alcohol, a botulinum toxin, etc. An endogenous toxic substances includes reactive oxygen species, neurotransmitter substances such as glutamate, etc., and abnormal proteins. A neuroprotective action can be easily measured by a person skilled in the relevant art. For example, after culturing nerve cells under various types of stress, such as a low-oxygen load, exposure to a neurotoxic substance, nutrient depletion, exposure to ultraviolet light, in culture media with the test substance (drug group) and culture media without the test substance (control group); measuring the number of viable cells and the number of dead cells in the media, and calculating the proportion of viable cells per total number of cells, one can judge that a test substance has a neuroprotective action, if the proportion of viable cells of the drug group is higher than the proportion of viable cells of the control group. In a more preferable aspect, a drug group can be compared to a positive control group to which a substance known to have a neuroprotective action such as IFG-1 or NGF, etc., has been added, and a neuroprotective action is determined by determining whether or not the drug group has a protective action equivalent to or greater than that of the positive control group. Another example includes determining the neuroprotective action by carrying out an in vivo animal study.

The neuroprotective agent comprises at least one peptide selected from the peptides according to the present invention. Peptides that can be included in such a neuroprotective agent includes, for example but not be limited to, peptides of sequences selected from a group consisting of SEQ ID NOS: 1 to 11.

In another situation, the present invention also relates to a pharmaceutical composition for treating or preventing nerve damage, containing a therapeutically effective dose of the abovementioned peptide or neuroprotective agent. Nerve damage can be treated by administering the pharmaceutical composition of the present invention to a patient having nerve damage; or nerve damage can be prevented by administering the pharmaceutical composition of the present invention to a patient with potential nerve damage. Moreover, the term "treat"/"Treatment" refers to preventing the worsening of the condition, maintaining the status quo of the condition. reducing or curing the condition, when damage or disease has occurred; and the term "prevent"/"prevention" refers to preventing the occurrence of damage or disease before it occurs.

A peptide, neuroprotective agent or pharmaceutical composition according to the present invention can be used in the method of treating or preventing nerve damage, and can be administered to a subject suffering from nerve damage. Such nerve damage refers to a condition caused by degeneration/cell death of nerve cells, in which the function of the nerve cells is damaged, and includes cerebrovascular disorders and neurodegenerative diseases.

Cerebrovascular disorders include a bleeding disorder such as a brain hemorrhage, a subarachnoid hemorrhage; and a disorder caused by an occlusion of a cerebral blood vessel such as a cerebrovascular blood clot, a cerebral infarction, a cerebral circulatory insufficiency, etc. In both bleeding disorders and occlusive disorders, nerve cells in the brain are in a hypoxic state, which causes cell death. Therefore, a peptide, a neuroprotective agent or a pharmaceutical composition according to the present invention can be administered for a therapeutic or preventive purpose for such cerebrovascular disorders.

Neurodegenerative diseases include Degenerative brain diseases and central neurodegenerative diseases such as, dementia, Parkinson's disease, spinocerebellar degeneration, Creutzfeldt-Jakob disease. Alzheimer's disease, Huntington's chorea, multiple sclerosis, mad cow disease, epilepsy, etc.; motor neuron degenerative diseases such as spinal progressive muscular atrophy, amyotrophic lateral sclerosis, spinal and bulbar muscular atrophy; and sensory neurodegenerative diseases. Sensory neurodegenerative diseases includes degenerative diseases of optic nerves, auditory nerves, touch sensory nerve, taste nerve, and olfactory nerve. Degenerative disease of optic nerves includes glaucoma, retinal pigmentary degeneration, age-related macular degeneration, diabetic retinopathy, etc., and auditory nerve degenerative diseases includes hearing loss.

A peptide, neuroprotective agent or pharmaceutical composition according to the present invention is provided in a dosage form suited to parenteral administration or oral administration, but from the perspective of using it as a peptide formulation, a parenteral administration would be preferable. Examples of parenteral administration include intravenous, intra-arterial, subcutaneous, topical, intraperitoneal, intramuscular, intranasal, percutaneous, transmucosal, intrathecal, rectal, intramuscular, intracerebral, intrathecal, subarachnoid, epidural, eye drop instillation, ear drop instillation, nasal drop instillation, and intraocular administration. More specifically, subconjunctival administration, sub-tenon administration, and intravitreal administration can be mentioned as routes of intraocular administration. A neuroprotective agent according to the present invention can be formulated in a suitable dosage form according to the route of administration, for example, in any farm: e.g. eye drops, an injectable formulation, powder formulation, infusion formulation, granular formulation, tablet, suppository, etc. For parenteral administration, eye drops, injectable formulation, infusion formulation, a powder medicine for extemporaneous preparation, etc. are preferable. Examples of intraocularly administered formulation that can be mentioned include an intravitreally injectable formulation, a subconjunctivally injectable formulation, and a sub-tenon injectable formulation. Moreover, these pharmaceutical formulations may contain various pharmaceutically acceptable adjuvants, i.e. a carrier or other auxiliary agent, e.g. an additive such as a stabilizing agent, a preservative, a soothing agent, an emulsifier, etc. Moreover, it can also be used in combination with another medicine having a neuroprotective action.

The entire contents of all literature cited in the present specification are incorporated herein by citation.

The purpose of the Examples of the present invention described below is only to exemplify the present invention, and they do not limit the technical scope of the present invention. The technical scope of the present invention shall be limited by the wording of the claims alone. The present invention may be changed on condition that such change does not depart from the spirit of the present invention: For example, an addition or substitution to or a deletion of a constituent feature of the invention can be realized.

EXAMPLES

Test Example 1

Synthesis of Peptides

Physiologically active peptides of the present invention, which were used in tests described below, were solid-phase synthesized by an Fmoc method using a peptide synthesizer (model: PSSM-8 manufactured by Shimadzu Corporation). The synthesized peptides were analyzed by mass spectrometry (MALDITOF), and as shown in the table below, the measurement values were highly consistent with the theoretical values.

TABLE 5

| | Mass spectrometry | | |
|---|---|---|---|
| | Theoretical value | Measurement value | Sequence |
| Peptide 1 | 1636.8 | 1636.6 | HPPPPPFQNQQRPP (SEQ ID NO: 3) |
| Peptide 2 | 1286.4 | 1286.5 | HPPPPPFQNQQ (SEQ ID NO: 6) |
| Peptide 3 | 916.0 | 916.6 | HPPPPPFQ (SEQ ID NO: 9) |
| Peptide 4 | 624.7 | 625.2 | QQRPP (SEQ ID NO: 14) |

Test Example 2

The Protective Effect of the Peptide against Cell Death of Human Neuroblastoma (SH-SV5Y cells) from Hypoxia 1. Cell Culture
SH-SY5Y cells (ATCC) were sustainably cultured in a DMEM/F12 medium (Invitrogen, 11330-032) supplemented with a 10% serum (Invitrogen, 10062-147) under the condition of 37° C. and 5% $CO_2$.
2. Hypoxia-Induced Cell Death Assay
The cells were seeded on a 96-well plate (Iwaki, 3860-096) at a density of $2 \times 10^4$ cells/100 μl/well. The following day the medium was replaced with a DMEM/F12 medium comprising a 1% serum and 10 μM of a retinoic acid (Wako, 302-79-4) and differentiated by incubation for 2 days. After replacing the medium with a glucose-free DMEM medium supplemented with 100 nM of Peptide 1, a hypoxia state ($O_2$ concentration of 0.1% or less) was induced by putting the plate in an Anaero Pack rectangular jar with Anaero Pack Kenki 5% (Mitsubishi Gas Chemical Company, Inc., A-07) with hermetically sealing, and culturing at 37° C. After culturing for 24 hours in the hypoxia state, the cell-death inhibiting rate by tire peptide was calculated by measuring the amount of LDH in the cells and the medium, using an LDH cytotoxicity detection kit (Takara. MK401). Moreover, 100 nM of ail IGF-1 was used as a positive control in the experiment. IGF-1 has a protective effect against nerve cell death (Mol. Cell Neurosci, 2011.47 (3), 181-190).

3. Test Results

As shown in tire table below, 100 uM of Peptide 1 significantly suppressed the cell death from hypoxia of the neuroblastoma SH-SY5Y cells. From this result, it was ascertained that Peptide 1, which is a partial sequence of proline-rich-protein 4 identified in tears, exhibits a neuroprotective action. The rate of suppression of cell death was higher than the rate detected for IGF-1, an existing nerve growth factor.

TABLE 6

|  | Cell lethality (%) |
|---|---|
| Peptide 1 (100 nM) | 86.1 ± 43.9* |
| IGF-1 (100 nM) | 88.1 ± 8.3* |
| Vehicle | 0.0 ± 16.5* |

The mean ± standard error (n = 3)
*p < 0.05 (compared to the vehicle. t-test)

Test Example 3

The Protective Effect of the Peptide against Cell Death of Rat Retinal Ganglion Cells (ROC) from Hypoxia 1. Preparation of the Rat Retinal Ganglion Cells Retinal ganglion cells were isolated by a magnetic activated cell sorting method (MACS). Retinas were harvested from neonatal rats (Sic: Sprague-Dawley, 7-day old) and the tissue was dissociated using a Neural Tissue Dissociation Kit (Milteuyi Biotec. 130-094-802). Then, using a Retinal Ganglion Cell Isolation Kit (Milteuyi Biotec. 130-096-209), the endothelial cells and microglia were removed, and a positive selection for CD90.1⁺ RGC was carried out by means of CD90. IMicroBeads. The test was carried out with the approval of the Animal Test Ethics Committee based on the Act on Welfare and Management of Animals (Act number 105 of Oct. 1, 1973, last revision: Act number 38 of June 12, 2013), etc.

2. Cell Culture

After suspending the isolated RGC in a neurobasal medium (Gibco Corporation. 12348-017) containing a B27 supplement (Invitrogen, 0080085-SA), ImM of L-glutamine (Gibco, 25030), 50 ng/ml of BDNF (Peprotech, 25-02). 50ng/ml of CNTF (Peprotech, 450-50) and 5 μm of Forskolin (Sigma, F6886), they were seeded on a 96-well plate (Coming, 354596), which was coated with poly-D-lysine/laminin, at a density of $5×10^3$ cells/100 μl/well, and incubated at 37° C. and 5% $CO_2$ for three days.

3. Hypoxia-Induced Cell Death Assay

After having replaced the media with neurobasal media comprising a B27 supplement, 1 mM of L-glutamine 50 and each peptide, a hypoxia state ($O_2$ concentration of 0.1% or less) was induced by putting the plate in an Anaero Pack rectangular jar with Anaero Pack Kenki 5% (Mitsubishi Gas Chemical Company, Inc., A-07) with hermetically sealing, and incubating at 37° C. After incubating for 24 hours under hypoxia condition, Calcein-AM and Ethidium homodimer (Invitrogen, L3224) were added to the media. As a result of staining the cells, it was possible to distinguish between the viable cells and the dead cells. The number of viable cells and dead cells were measured using an Image Pro plus, and the rate of viability was given as "the proportion of the viable cell count relative to the total cell count."

4. Test Results

As shown in the table below, Peptides 1 to 4 significantly suppressed the cell death from hypoxia. These results suggest that Peptide 4 is the peptide with minimal active sequence.

TABLE 7

|  | Rate of cell-death suppression (%) |
|---|---|
| Peptide 1 (100 nM) | 25.4 ± 7.8* |
| Peptide 2 (100 nM) | 26.4 ± 4.8* |
| Peptide 3 (100 nM) | 27.2 ± 6.6** |
| Peptide 4 (100 nM) | 31.1 ± 7.8** |
| Vehicle | 0.0 ± 7.4 |

The mean value ± standard error (n = 14-19)
*p < 0.05
**p < 0.01 (compared to the vehicle. t-test)

Test Example 4

The Protective Effect of Proline-Rich Protein 4 (PRP4) against Cell Death of Rat RETINAL GANGLION CELLS (RGC) from Hypoxia 1. Preparation of the Rat Retinal Ganglion Cells and Cell Incubation The isolation and incubation of RGC were performed by the same methods as for Test Example 3-1. and 2.

2. Hypoxia-Induced Cell Death Assay

Commercially available PRP4 (Abnova. H0011272-Q01) having the sequence of SEQ ID NO: 2, was used for Peptide 5. The evaluation of Peptide 5 was carried out by the same evaluation method as used for Test Example 3-3.

3. Test Results

As shown in the table below. Peptide 5 significantly suppressed the cell death from hypoxia.

TABLE 8

|  | Rate of cell-death suppression (%) |
|---|---|
| Peptide 5 (10 nM) | 66.2 ± 14.4* |
| Vehicle | 0.0 ± 21.9 |

The mean value ± standard error (n = 12 to 18)
*p < 0.05 (compared to the vehicle. t-test)

Test Example 5

Test of the Stability of Peptide 1 in a Vitreous Humor Solution (Two) rabbits were euthanized by intravenous administration of 5 ml of a pentobarbital sodium solution, and then their eyeballs were removed An incision was made in the equatorial region of each eyeball, and the vitreous humor solution was harvested from each eyeball using a syringe (18G injection needle) at the site of incision. The mixed vitreous humor solution was filtered with a cell strainer (40 μm) and the filtrate was used as the vitreous humor solution for the stability tests. 600 μl of the vitreous humor solution was mixed with 1.2 μl of a Primocin at a concentration of 50 mg/ml and the resultant solution was used as sample solution. 270 μl of the sample solution and 1 nM of Peptide 1 in a 30 d aqueous solution were mixed and the resultant mixture was used as the test sample. The test sample was incubated at 37° C. 7 days later, 30 μl of the test sample was collected and mixed with 200 μl of a 1 N acetic acid. The resultant mixture was boiled at 100μ C. for 10 minutes and that mixture was then used for the analysis samples. The analysis samples were stored frozen at −20° C. until it was time to take readings using them. After they were melted, they were put through a centrifugal treatment (15000×g) at 4° C. for 20 minutes. Then, the concentration of Peptide 1 in each sample was analyzed using liquid chromatography. The concentrations were calculated from the area values obtained using the external standard method. The conditions of analysis of the liquid chromatography were as outlined below.

<Conditions of Analysis of the Liquid Chromatography>
Mobile phase A: 10% acetonitrile+0.1% trifluoro acetic acid
Mobile phase B: 60% acetonitrile+0.095% trifluoro acetic acid
Gradient analysis: B conc. 0% to 50% if minutes
Flow rate: 1 ml/minute

| Column: YMC-Pack | ODS-AQ S-3 μm, 12 nm | 150 × 4.6 mm |
|---|---|---|

I.D. AQ12S03-1546WT
System: Shimadzu LC-20A
Column oven: 40° C.

The residual rate of Peptide 1 after 7 days' incubation with the vitreous humor solution is shown in Table 9. The residual rate was calculated using the following formula:

Residual rate=(the concentration of peptide after 7 days' incubation/the concentration of peptide in the test samples immediately after they were prepared)×100    [Formula 1]

TABLE 9

| | Residual ratio (%) |
|---|---|
| Peptide 1 | 98.4 |

This result established the fact that Peptide 1 is stable in a vitreous humor solution.

Formulation Examples

A pharmaceutical product containing a peptide according to the present invention as an active ingredient can be manufactured by formulations such as the following for example. The agent of the present invention will be described in detail, referring to the formulation examples, but the present invention is not limited to these formulation examples alone.

1. Capsule Medicine

| | |
|---|---|
| (1) Peptide 1 | 40 mg |
| (2) lactose | 70 mg |
| (3) microcrystalline cellulose | 9 mg |
| (4) magnesium stearate | 1 mg |
| 1 capsule | 120 mg |

Mix the full amounts of (1), (2), and (3) and half the amount of (4) and then granulate the mixture. Add the remaining amount of (4) to the granulated mixture and encapsulate the whole resultant mixture in a gelatin capsule.

2. Tablet

| | |
|---|---|
| (1) Peptide 4 | 40 mg |
| (2) lactose | 58 mg |
| (3) corn starch | 18 mg |
| (4) microcrystalline cellulose | 3.5 mg |
| (5) magnesium stearate | 0.5 mg |
| 1 tablet | 120 mg |

Mix the full amounts of (1), (2), and (3), two thirds of (4) and half of (5) then granulate the mixture. Add the remaining amounts of (4) and (5) to the granulated mixture and compress the resultant mixture into a tablet form.

2. Vitreous Humor Injection Solution

| Content of 1 ml | |
|---|---|
| (1) Peptide 1 | 40 mg |
| (2) purified white sugar | 50 mg |
| (3) sodium chloride | 2.34 mg |
| (4) polysorbate 80 | q.s. |
| (5) disodium hydrogen phosphate | q.s. |
| (6) sodium dihydrogen phosphate | q.s. |
| (7) sterilized purified water | q.s. |

Prepare a vitreous humor injection solution by dissolving ingredients (1) to (6) in the sterilized purified water (7).

Sequence Listing

The invention claimed is:

1. A peptide consisting of: (a) the amino acid sequence of HPPPPPFQNQQRPP (SEQ ID NO: 3); or (b) a terminal-deleted sequence thereof which is a sequence derived from SEQ ID NO: 3 by deletion of 1 to 6 amino acids from the C-terminal thereof,
wherein the peptide consisting of the terminal-deleted sequence has a neuroprotective action.

2. A peptide consisting of the amino acid sequence of HPPPPPFQ (SEQ ID NO: 9) and wherein the peptide has a neuroprotective action.

3. A peptide consisting of the amino acid sequence of HPPPPPFQNQQ (SEQ ID NO: 6) and wherein the peptide has a neuroprotective action.

4. A peptide consisting of the amino acid sequence of HPPPPPFQNQQRPP (SEQ ID NO: 3)
wherein the peptide has a neuroprotective action.

* * * * *